United States Patent [19]
Gill

[11] Patent Number: 5,756,537
[45] Date of Patent: May 26, 1998

[54] REGIME FOR PACLITAXEL IN KAPOSI'S SARCOMA PATIENTS

[75] Inventor: Parkash S. Gill, Agoura Hills, Calif.

[73] Assignee: Parkash S. Gill, M.D., Inc., Agoura Hills, Calif.

[21] Appl. No.: 745,573

[22] Filed: Nov. 8, 1996

[51] Int. Cl.$^6$ .................... A01N 43/02; A01N 43/32; A01N 43/64; A61K 38/00
[52] U.S. Cl. .................. 514/449; 514/450; 514/451; 514/452; 514/359; 514/383; 514/8
[58] Field of Search .................... 514/449, 450, 514/451, 452, 359, 383, 8

[56] References Cited

U.S. PATENT DOCUMENTS 5,565,478  10/1996  Kohn et al. .......................... 514/383

OTHER PUBLICATIONS

Straubinger et al. *JNCI* 15:69–78, (1993).
Gianni, et al., *J Clin. Oncol.*, 13(1):180–90 (1995).
Saville, et al., *Blood*, 84(10 Suppl 1):S103, Abstract 163 (1994).
Wiernak, et al., *J. Clin. Oncol.*, 5:1232–9 (1987).
Huizing, et al., *J Clin. Oncol.* 11(11):2127–2135 (1993).
Eisenhauer et al., *J Clin. Oncol.* 12: 2654–2666 (1994).
McGuire, et al. *Ann. Int. Med.*, 111:273–279 (1989).
Holmes, et al. *J. Natl. Cancer Inst.*, 83:1797–1805 (1991).
Kohn et al., *J. Natl. Cancer Inst.*, 86:18–24 (1994).
Kohn, et al., *American Society for Clinical Oncology*, 12, Abstract 814 (1993).
Donehower, et al., *Cancer Treatment Reports* 71(12):1171–7 (1987).
Brown, et al., *J Clin. Oncol.*, 9(7):1261–7 (1991).
Saville, et al., *Lancet* 346(8966):26–8 (1995).

*Primary Examiner*—Marian C. Knode
*Assistant Examiner*—Ali R. Salimi
*Attorney, Agent, or Firm*—Townsend and Townsend and Crew LLP

[57] ABSTRACT

This invention provides for novel dose regimen of paclitaxel to treat Kaposi's sarcoma. Unlike current paclitaxel therapy protocols, the claimed dosages are lower yet surprisingly as effective in regression of KS tumors. In addition, the lower doses are accompanied with fewer incidents of undesired side effects. The effectiveness of low doses of paclitaxel as well as fewer and less debilitating side effects, makes this therapy protocol the first that can be used for long term and as maintenance therapy in the management of patients with Kaposi's sarcoma.

14 Claims, 2 Drawing Sheets

REGIME FOR PACLITAXEL IN KAPOSI'S SARCOMA PATIENTS

BACKGROUND OF THE INVENTION

Paclitaxel therapy has been used to treat Kaposi's sarcoma patients. However, at dosage levels suggested by the prior art, there are unwanted hematological side effects and regression of tumors after cessation of treatment is common. Thus, the prior art suggests that long term paclitaxel treatment would be problematic in the management of Kaposi's sarcoma.

This invention provides for novel dose regimes of paclitaxel to treat Kaposi's sarcoma (KS). Unlike the dosage regimes described as efficacious in the prior art, the lower $AUC_{(0 \to \infty)}$ of paclitaxel therapy claimed in this invention is surprisingly effective.

Kaposi's sarcoma may appear in three different classes of individuals. Classic Kaposi's sarcoma is a rare, indolent, cancer of mainly elderly men of Jewish or Mediterranean origin (Lospalleti, M., et al., *Dermatology*, 191(2): 104-8 (1995)). Endemic Kaposi's sarcoma (EKS) affects elderly and young Africans, particularly Bantus. EKS can become particularly aggressive after a long period of quiescence (Safai, B., *Semin Oncol*, 2 (Suppl 3): -12 (1987)). HIV-associated Kaposi's sarcoma is an aggressive cancer found as an opportunistic disease related to infection with HIV (Wahman, A., et al., *Epidemiol Rev.*, 13: 178-9 (1991)). In all of the above types of Kaposi's sarcoma, a compromised immune system is indicated.

The HIV-related form of Kaposi's sarcoma (AIDS-KS) most frequently presents with cutaneous lesions. Occasionally, cases present with lymph node or visceral KS only. Mucosal involvement of the oral cavity is the second most common site of disease. The tumor lesions are noted frequently on the palate, and gums and can cause tooth loss, pain and ulceration (Paredes, J., J. *Acquir Immune Defic Syndr Hum Retroviral*, 9(2): 138-44 (1995)).

Lymph node involvement is common with KS, however, the precise frequency is not known due to the lack of routine lymph node biopsy in AIDS-KS. Visceral involvement occurs frequently (in nearly 50% of the cases) especially in patients with advanced or cutaneous disease. Advanced gastrointestinal KS can cause enteropathy, diarrhea, bleeding, obstruction and death.

Pulmonary involvement is common and significant pulmonary KS occurs in nearly 20% of the cases. The overall time of survival of patients with symptomatic pulmonary KS is less than 6 months. Nearly every organ can be involved with KS, including liver, spleen, pancreas, omentum, heart, pericardium, etc.

The treatment of AIDS-KS is at best palliative. Decisions regarding the type of treatment should be based on a number of parameters. These include the tumor burden, local complications such as tumor associated edema, ulceration, pain and visceral involvement. In addition bone marrow function, immunologic status, especially CD4 lymphocyte count, concurrent opportunistic infections and medications predict the ability to deliver certain drugs, and outcome to therapy. Localized KS can be managed with local therapy including radiation therapy. Radiation therapy produces a high response rate with reduction in the tumor nodules and resolution of pain. Radiation of mucosal tissues of HIV infected patients can cause increased risk for local toxicity such as mucositis and thus should be delivered at lower daily dose. Other options for the cosmetic treatment of localized disease include cryotherapy, photodynamic therapy, intralesional vinblastine, and intralesional sclerosing agents. However, advanced cutaneous disease correlates with the risk for visceral involvement. Therefore, major emphasis should be placed on systemic therapy.

Because of the progressiveness of cutaneous KS, especially with local complications of pain, edema, and ulceration, symptomatic visceral KS requires therapy which results in rapid response. The active single agents utilized in KS therapy include vinca alkaloids (vincristine, vinblastine), anthracyclines (doxorubicin, daunorubicin), bleomycin, and etoposide. KS is not a curable disease despite the best possible therapy available, therefore, the development of other agents with activity in KS and a toxicity profile that allows for prolonged use are needed. Paclitaxel has been proven to be one such agent. The use of novel dose and schedule of paclitaxel as shown in this invention demonstrates its surprising safety during prolonged use. Accordingly paclitaxel is shown suitable for patients with AIDS-KS including those who otherwise could not tolerate toxic agents.

SUMMARY OF THE INVENTION

The current invention discloses methods for treating Kaposi's sarcoma with long-term administration of paclitaxel (Taxol®, Bristol-Myers Squibb Co.) at therapeutic doses that avoid adverse side effects common with current therapy regimes. Specifically, this invention demonstrates that at peak levels of paclitaxel between 0.1–1 μvM, KS lesions will respond and complete regression is possible. This invention also demonstrates by maintaining a threshold level of 0.1–1 μM paclitaxel for shorter periods of time than that described in the prior art and by maintaining an AUC $_{(0 \to \infty)}$ of 1–4 μM/hour of paclitaxel, one can reduce neutropenia and other side effects so that the drug can be administered for treatment and as a maintenance drug for extended periods.

More particularly this invention provides for a method of treating Kaposi's sarcoma patients comprising the administration of paclitaxel at 35–100 mg/m$^2$ in a less than three hour bolus every 10–16 days, preferably in a 1.5–3 hour bolus.

The mode or route of administration can be parenteral: e.g., intravenous; intraperitoneal; subcutaneous; oral; or topical for cutaneous tumors. The median time to achieve partial response is 6–10 weeks or 3–5 cycles. The time to partial response depends on whether the patient has previously received cytotoxic therapy. The median duration of response is greater than 20 weeks with a range of up to 60 weeks.

BRIEF DESCRIPTION OF THE FIGURES

FIG. 1 details the effects of paclitaxel on cell proliferation assays. Paclitaxel at various concentrations was added to cell cultures for 5–6 days. At that time surviving cells were assayed by cell counting.

FIG. 2 details the effect of paclitaxel on KS Y-1 in vivo. Nude mice (n=6) were implanted with KS Y-1 cells and then treated with paclitaxel on days 1, 3 and 5. Tumor size was measured on days 14 and 21.

DETAILED DESCRIPTION OF THE INVENTION

Definitions

Figure 1A:
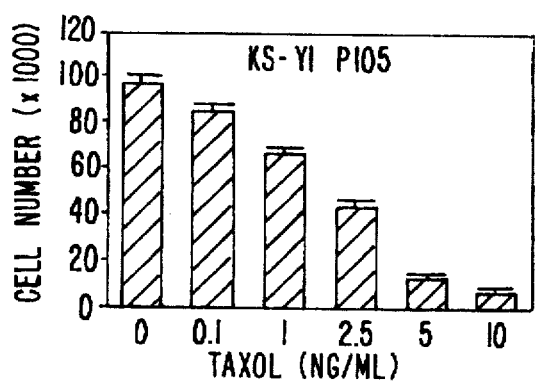
FIG. 1.
Figure 1B:
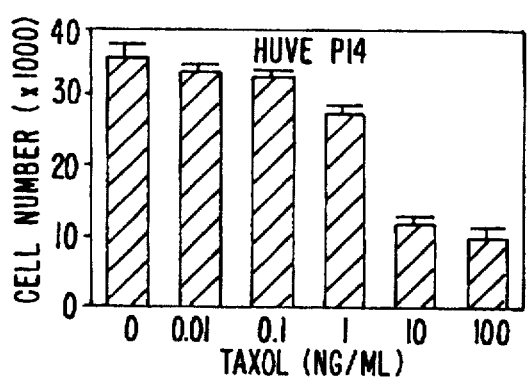
Figure 1C:
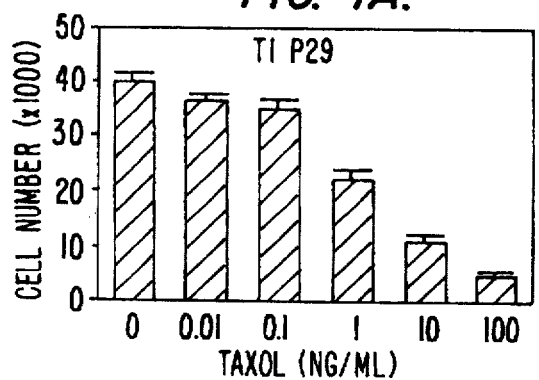
Figure 1D:
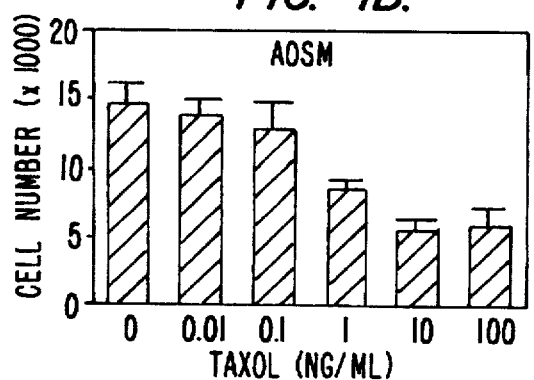

"Dose intensity" means the amount of drug administered per infusion per cycle.

"Bolus" means a one time injection.

"Recycling" means repetitive infusions of paclitaxel at the indicated time interval, usually 10–16 days.

"Response" means a halt in the progression of KS lesions and/or a decrease in tumor size without accompanying unwanted side effects.

"Partial response" means a complete flattening of more than 50% of the raised lesions lasting for four weeks or more.

"Remission" means "Complete Clinical Remission" or a flattening all raised lesions lasting for four or more weeks. It also means, histopathologically, disappearance of KS spindle cells from areas where lesions once were.

"Pharmacologically acceptable carrier" means any chemical approved for use by the Food and Drug Administration as part of a drug formulation.

"Peak levels" means the maximum level of paclitaxel present in the blood during a treatment cycle. Typically, this level will be achieved shortly after the infusion of paclitaxel has ended.

"Area under the curve (AUC)" refers to the area under a pharmacokinetics curve where the abscissa is defined by the time and the ordinate by the serum levels of paclitaxel. This area is calculated using the equation:

$$C_T = \sum_{i=1}^{N} C_i \times e^{(-\lambda_i t)}$$

where $\lambda_i$ is the exponent of the i-th exponential term, and $C_i$ is the initial concentration of the i-th component of the curve. Curve fitting with this model yields the parameters $C_1$, $C_2$, $C_3$ $\lambda_1$, $\lambda_2$ and $\lambda_3$. The half-lives ($t_{1/2}$s) are calculated from the equations $t_{1/2}(\alpha)=0.693/\lambda_1$, $t_{1/2}(\beta)=0.693/\lambda_2$ and $t_{1/2}(\gamma)=0.693/\lambda_3$. The total area under the curve ($AUC_{0 \to \infty}$) is calculated using the linear trapezoidal method with extrapolation of the terminal phase to infinity ($C_{last}/\lambda_3$), where $C_{last}$ is the last measured concentration. Individual responses to paclitaxel may vary depending on body composition and AUC represents a statistical average using people of normal size and body weight.

Introduction

In vitro studies confirm that KS cells are as sensitive to paclitaxel as human ovarian cell lines (see Example 1 and Straubinger et al. *JNCI* 15:69–78 (1993)). Therefore, one would expect a clinical response to paclitaxel similar to that seen with ovarian and breast cancer. In ovarian cancer, typically the dose is 135–175 mg/m² and in breast cancer, the dose is 225 mg/M² repeated every three weeks or even more infrequently, if hematologic recovery is not achieved (see, Gianni, et al., *J Clin. Oncol.*, 13(1):180-90 (1995)). However, based on the clinical evidence presented in this invention, KS can be treated by paclitaxel at lower than predicted doses, in particular from 35–100 mg/m². Previously, Saville and his colleagues at the NCI initiated a phase I clinical trial at 105 mg/M² of paclitaxel (Saville, et al, Blood, 84(10 Suppl 1):S103, Abstract 163 (1994)). However, once the safety of paclitaxel at this dose was demonstrated, they increased the dose to 135 mg/M² to 175 mg/M² over three hours, recycled every 21 days, dosages as suggested by trials with breast and ovarian tumors. And similar to trials with ovarian and breast cancer, Saville, et al. observed increased incidents of myelosuppression.

This invention, which incorporates lower doses of paclitaxel, over a faster recycling of doses, is advantageous over Saville et al. because the decreased infusion time allows therapeutic peak levels of paclitaxel to be achieved but sustained over a shorter period of time. It is believed that a threshold peak level of 0.1 µM paclitaxel is necessary for pharmaceutical effect (Wiernak, et al., *J. Clin. Oncol.*, 5:1232-9 (1987). However, peak dose levels of greater than 0.05 µM over extended periods of time have also been implicated in adverse hematological side effects (Gianni, et al. Huizing, et al., *J Clin. Oncol.* 11(11):2127–2135 (1993), Eisenhauer et al., *J Clin. Oncol.* 12: 2654–2666 (1994)).

Paclitaxel and other antineoplastic drugs act as bone marrow suppressors. Bone marrow suppression leads to anemia, eosinophilia, neutropenia and thrombocytopenia. The above pathological conditions plus non-hematologic side effects, such as transient alopecia, nausea, diarrhea, myalgia and neuropathy commonly accompany antineoplasts.

A general trend present in the prior art is to increase the duration of infusion while decreasing mg/m². The purpose for lengthening exposure is to lessen the immunologic reactions typical with paclitaxel therapy. However, this results in an increased overall exposure to paclitaxel, and it is the duration of exposure above a certain level in the blood that induces neutropenia. To better explain this invention, a comparison of paclitaxel to acetaminophen is useful.

Acetaminophen produces toxic effects upon overdose due to toxic metabolites. In contrast, paclitaxel apparently falls into a different category of drug which produces toxic effects due to prolonged exposure. Examples of other such compounds are aminoglycosides and methotrexate.

By following the disclosed protocol of less paclitaxel and more frequent infusions, one sees dramatic remission of KS and striking elimination of side effects. In view of the suggested protocols of the prior art which maintained high levels of exposure while infusing every 21 days, our approach to treating KS patients is both surprisingly effective and counterintuitive.

Paclitaxel pharmacology

Paclitaxel (Taxol®) is a diterpene isolated from the bark of the Western (Pacific) yew, *Taxus brevifolia* and is representative of a new class of therapeutic agent having a taxane ring system. Paclitaxel and its analogs have been produced by partial synthesis from 10-deacetylbaccatin III, a precursor obtained from yew needles and twigs, and by total synthesis. See Holton, et al., *J. Am. Chem. Soc.* 116:1597–1601 (1994) and Nicolaou, et al., *Nature* 367:630 (1994). The antitumor activity of paclitaxel is due to a promotion of microtubule polymerization. See Kumar, N., *J. Biol. Chem.* 256:10435–10441 (1981); Rowinsky, et al., *J. Natl. Cancer Inst.*, 82:1247–1259 (1990); and Schiff, et al., *Nature*, 277:655–667 (1979). Paclitaxel has now demonstrated efficacy in several human tumors in clinical trials, including breast and ovarian cancers. See McGuire, et al., *Ann. Int. Med.*, 111:273–279 (1989); Holmes, et al., *J. Natl. Cancer Inst.*, 83:1797–1805 (1991); Kohn et al., *J. Natl. Cancer Inst.*, 86:18–24 (1994); and Kohn, et al., *American Society for Clinical Oncology*, 12 (1993).

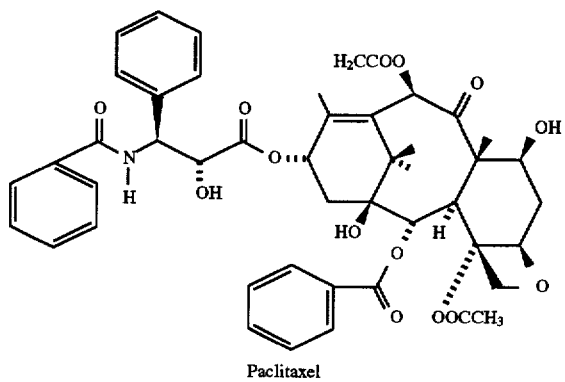

Paclitaxel

Paclitaxel

Typically, paclitaxel is provided from the manufacturer dissolved in a 1:1 solution of ethanol and polyethoxylated castor oil (Cremaphor EL). The oil used to solubilize the paclitaxel may cause anaphylaxis during injection. To prevent this allergic response, the patient should be pretreated with glucocorticoids and antihistamines. The most commonly used are dexamethasone, cimetidine and diphenhydramine.

The paclitaxel compositions of the present invention will also contain a pharmaceutically acceptable carrier. Pharmaceutically acceptable carriers are well known to those who are skilled in the art. The choice of a carrier will be determined by the particular method used to administer the paclitaxel. Accordingly, there is a wide variety of suitable formulations of the pharmaceutical compositions of the present invention. Some of the carriers used in these formulations include water, saline and PEG 400 (for oral administration); propellants such as dichlorodifluoromethane, propane or nitrogen (for inhalation administration); creams and emollients for topical administration; and natural and aqueous or non-aqueous isotonic sterile injection solutions, such as Cremophor EL (for intravenous, intramuscular, intradermal, intraperitoneal, and subcutaneous administration). Additionally, the formulations may contain detergents, such as Tween 80.

Paclitaxel may also be administered encapsulated in liposomes, pharmaceutical delivery vehicles wherein the active ingredient is contained either dispersed or variously present in corpuscles consisting of aqueous concentric layers adherent to lipidic layers.

A variety of methods are available for preparing liposomes as described in, e.g., Szoka et al., *Ann. Rev. Biophys. Bioeng.* 9:467 (1980), U.S. Pat. Nos. 4,235,871, 4,501,728, 4,837,028, the text *Liposomes*, Marc J. Ostro, ed., Chapter 1, Marcel Dekker, Inc., New York (1983), and Hope, et al., *Chem. Phys. Lip.* 40:89 (1986), all of which are incorporated herein by reference.

Micelles containing paclitaxel can be prepared by methods which are well known to one of skill in the art. For example, see U.S. Pat. No. 5,534,499 herein incorporated by reference.

In addition to liposomes and micelles, paclitaxel can be administered as an emulsion or within a protein or other polymeric shell linked by disulfide bonds (U.S. Pat. No. 5,560,933(herein incorporated by reference)). Both paclitaxel containing emulsions and polymeric shells can be produced through sonication.

Most preferably, paclitaxel is administered intravenously in an aqueous solution. Such aqueous solutions can include: 0.9% sodium chloride injectable, 5% dextrose injectable, 5% dextrose in combination with 0.9% sodium chloride injectable, or 5% Ringers solution, to a final concentration of 0.3 to 1.3 mg/mL.

Paclitaxel has been studied in a variety of disease states with activity in breast and ovarian cancer. Preclinical and human trials suggest that minimal doses of 135 mg/m$^2$ and generally around 175–200 mg/m$^2$ are required to obtain responses when given over 3–96 hour infusion, every 3–4 weeks (Kohn, et al., U.S. Pat. No. 5,565,478, Donehower, et al.,*Cancer Treatment Reports* 71(12):1171-7(1987), McGuire, et al., *Ann. Int. Med.* 111:273-9 (1989), Brown, et al., *J Clin. Oncol.*, 9(7):1261-7 (1991), Huizing, et al, and Eisenhouer, et al.). Similar findings have been reported in patients with AIDS-KS (Saville, et al., *Lancet* 346(8966) :26-8 (1995)). In one study, after treatment with 135 mg/m$^2$, if the patient did not develop hematological side effects, the dosage was increased to 175 mg/m$^2$.

In ovarian and breast cancer treatment, the cause of the increased hematological side effects has been postulated to be prolonged peak levels of paclitaxel. In one study, it was found that if peak levels of paclitaxel exceeded 0.05 µM over extended periods of time, the incidence and severity of neutropenia increased (Gianni et al.). Another indicator of increased myelosuppresssion is an increased AUC$_{0 \to \infty}$. Huizing, et al found that an AUC$_{(0 \to \infty)}$ of about 8 to 12 µM/hour with a 3 hour infusion of paclitaxel led to increased side effects in ovarian cancer patients The same increased hematological side effects would be expected to be observed in AIDS-KS patients. In the AIDS-KS patient, bone marrow function is already compromised, due to the HIV infection, other infections and factors such as cytokines and interleukins produced in response to these infections. Furthermore, these patients are on numerous other cytotoxic agents that severely inhibit bone marrow function and thus put them at risk for secondary infections. As such, many of these patients require hematopoietic growth factor support. Therefore long term treatment at previously disclosed doses and schedules of drug delivery based on ovarian cancer may not be the best treatment option for KS. A lower dose intensity but quicker cycling in patients with AIDS-KS who were either previously treated extensively with chemotherapy and had no other treatment options or were not previously treated may provide better treatment of their disease.

Administration of Paclitaxel

The administration of paclitaxel in accordance with this invention requires a range of 35–100 mg/m$^2$ in a 3 hour bolus every 10–16 days. This leads to an estimated desired peak paclitaxel level of 0.1–1 µM. To decrease the side effects that accompany paclitaxel therapy, the peak levels need to be kept to a minimum and the AUC$_{(0 \to \infty)}$ kept below 8 µM/hour. By keeping the initial doses of paclitaxel in the range of 50–100 mg/m$^2$ and infusing in a three hour bolus, the length of time peak levels are achieved would be expected to be less than 15 hours (see, Gianni, et al.) and the AUC$_{(0 \to \infty)}$ would be between 1–4 µM/hour. Surprisingly, this decreased exposure to paclitaxel is effective in KS patients. After the patient has responded to the paclitaxel therapy, he or she can be placed on maintenance therapy of 35–50 mg/m$^2$ every 10–16 days. Typically, maintenance therapy is maintained for a minimum of 3-5 cycles. The AUC$_{(0 \to \infty)}$ for patients on these low doses is expected to be below that for the initial doses (1–4 µM/hour). The levels of paclitaxel can be measured in accordance with HPLC procedures well known to one of skill in the art (see, e.g., Gianni, et al. and Huizing, et al.).

Determining patient response in the treatment of Kaposi's sarcoma

Patient response to paclitaxel is measured by reduction and flattening of KS lesions. In addition, because of the unwanted side effects associated with paclitaxel therapy, patient response is also determined by degree of side effects observed.

All of the references cited herein are incorporated by reference. The following examples are provided by way of illustration only and not by way of limitation. Those of skill will readily recognize a variety of noncritical parameters which could be changed or modified to yield essentially similar results.

EXAMPLES

Example 1: Effects of Paclitaxel on Cell Proliferation Studies

KS has an unusual sensitivity to paclitaxel. This was established in the following in vitro assays.

AIDS-KS spindle cell lines were seeded at a density of $1.0 \times 10^4$ cells/well in a 24-well plate in KS medium. The cells were allowed to attach overnight, media was changed and the cells were treated with varying concentrations of paclitaxel on day 1 and 3. The cell counts were performed on day 5 or 6 using a Coulter Particulate Counter (Hialeah, Fla.). As can be seen from FIG. 1, the $IC_{50}$ of paclitaxel for KS Y-1 P105 was about 2-3 ng/mL.

Example 2: In vivo Model of the Effect of Paclitaxel on KS

Figure 2:
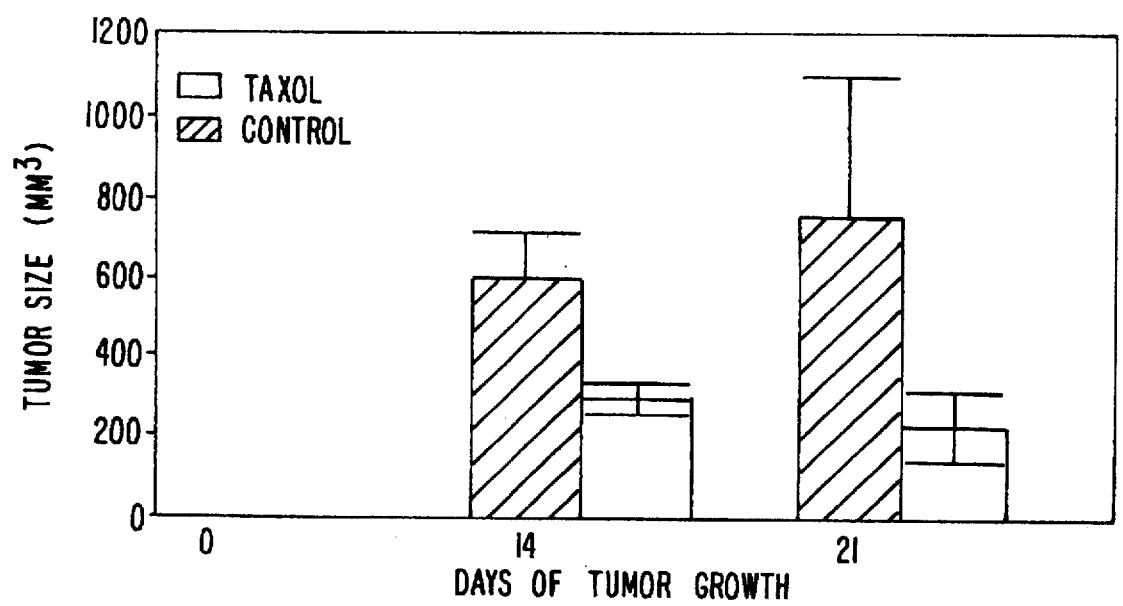
FIG. 2.

KS cell lines that propagate in the immunodeficient mouse were treated with paclitaxel. $1.0 \times 10^7$ cells were implanted subcutaneously in each Balbc/nu (Charles River) mouse. Animals were treated on days 1, 5 and 9 with paclitaxel intra peritoneally and the tumor size was measured on day 14 and 21 in treated and untreated animals. As can be seen in FIG. 2, tumor growth was markedly inhibited at doses of 10 mg/kg.

Example 3: 89 year old HIV-negative woman with KS

Patient JW, a 89 year old very fragile female presented with KS. Apparently the first site of disease was on the right foot with subsequent disease progression to all extremities, trunk, oral cavity, ears, eye lids, and genital organs. She also developed extensive edema of both lower extremities from KS. Other medical problems included hypertension, cardiac arrhythmia, congestive heart failure, and hypothyroidism.

Prior therapy included radiation therapy. The radiated areas included both feet and eye lids. Radiation induced partial resolution of the disease, however the edema did not respond. Furthermore, KS continued to progress at various sites. Cytotoxic chemotherapy was given with combination chemotherapy consisting of bleomycin, vincristine and adriamycin. Bleomycin induced pneumonitis with bilateral diffuse infiltration which responded partly to corticosteroid therapy.

On her insistence, she was first treated with human chorionic gonadotropin (HCG) at a dose of 5000 international units daily subcutaneously. However, she showed no response to this therapy. The tumor was very extensive and had extensive oozing including blood stained material, which was foul smelling, from the extremities. In addition, she had nodular pedunculated lesions over extensive regions of the body. She eventually agreed to receive chemotherapy with paclitaxel at a dose of 75 mg/m² given every two weeks as a three hour infusion. Premedication included dexamethasone, diphenhydramine, and cimetidine.

The toxicities experienced with this dose intensity of paclitaxel included skin itching and moderate hair loss. Most surprising was the lack of bone marrow suppression and accompanying neutropenia. The patient did not receive G-CSF and the therapy was delivered on schedule at the planned dose. The patient showed remarkable response with resolution of KS, oozing, foul smell and edema. The tumor resolved completely after five doses of paclitaxel in a period of eight weeks. A subsequent biopsy of the area of skin tumor showed lack of KS pathologically. The patient subsequently developed eczema of the legs was treated with local therapy with partial response. To ensure there was no relapse of KS, she received additional chemotherapy with paclitaxel alone and in combination with liposomally encapsulated doxorubicin for five months. The tumor remained in remission for eight months after the last combination chemotherapy treatment, then the patient developed relapse in the skin localized behind the left knee. In order to determine if lower doses of paclitaxel would induce a response, paclitaxel was started at a dose of 35 mg/m² to be given every two weeks.

After one cycle at 35 mg/m² paclitaxel, the disease remains stable. The results after the second cycle are still pending.

Example 4: 50 year old male

MB, a 50 year old male with Kaposi's sarcoma for one year was seen for treatment recommendation. The patient had extensive cutaneous KS with numerous tumor lesions. The patient had been treated with local therapy including laser therapy. As a result, he had numerous ulcerated tumor lesions. The patient was in severe pain and expressed a desire not to live. He was treated with intralesional HCG and topical cream of Vit D3 (Dovonex) with limited local response but progressive systemic KS.

Due to the lack of effective control of the extensive disease with local therapies, he was treated with liposomal daunorubicin (Doxil). He had a remarkable response. There was no evidence of new lesions and the existing lesions regressed rapidly. He wished to stop therapy in order to avoid treatment related toxicity. Five weeks after the last Doxil treatment, he had a rapid relapse, with development of numerous new lesions, in addition to the progression of previous lesions. He was thus retreated with Doxil, with the expectation that the tumors would respond again. However, instead of responding to the Doxil, new lesions developed.

He was treated with paclitaxel at a dose of 75 mg/m². He had a rapid response to the first dose of therapy. He did not develop any new lesions and the existing KS lesions began to regress rapidly. Due to very extensive disease, a representative area of tumor was monitored. He had 32 lesions on the left forearm prior to paclitaxel therapy, and all were raised. After single dose of paclitaxel, the lesion count was 12 with only two raised lesions. He, however, suffered severe hair loss. Because he had earlier clearly expressed that he did not wish to receive any therapy that might cause hair loss, it was decided to lower the paclitaxel dose intensity to 35 mg/m² every 2 weeks. He continued to respond favorably and three months after the initiation of the lower dose schedule, all KS lesions were completely flat (Clinical Complete Remission). In addition, the therapy was well tolerated, and his hair grew back while on therapy.

Example 5: Pilot Study of Ten Patients

A pilot study of 10 patients was conducted to determine tolerance to a below threshold dose intensity of paclitaxel. Seven of these ten patients had previously been treated with one or more previous regimens cytotoxic chemotherapy regimens. All were severely immunodeficient with history of opportunistic infection in six, advanced KS with numerous cutaneous KS lesions, involvement of visceral disease (which is generally fatal) in five. Paclitaxel was given at a dose of 100 mg/m$^2$ over 3 hr every 2 weeks after premedication with dexamethasone, cimetidine, and diphenhydramine. The treatment was well tolerated. Further, five of the ten patients achieved partial or complete response. Responses were observed in patients who had previously failed chemotherapy. Responses were also observed in patients who had otherwise fatal pulmonary disease. Similarly resolution of tumor associated edema was observed.

Example 6: Phase II Trial of Paclitaxel in Advanced AIDS-KS

We conducted a clinical trial of 55 patients. In this trial, patients were grouped into two strata: those who had received prior chemotherapy and those without prior chemotherapy. All patients had advanced KS defined by more than 25 cutaneous lesions, or presence of visceral disease, or lymphedema. Other eligibility criteria included adequate hepatic, renal, and bone marrow function defined as a bilirubin<2.0 mg/dl, GOT<x upper limit of normal, creatinine<2.1 mg/dl, granulocytes>1000/mm$^3$, and platelets>75,000/mm$^3$. Patients could not have had prior therapy for their KS within the last 2 weeks. The dosage and schedule was 100 mg/m$^2$ intravenously every 2 weeks.

The results are given by each strata. Strata 1 consisted of 35 patients who had previously been treated with chemotherapy (Tables 1–3). At time of study entry, 56% of patients were receiving concurrent antiretroviral therapy with AZT (16%) or other agents (40%). In addition, 28% were receiving concurrent myelosuppressive therapy with Cytovene (DHPG) for the treatment of cytomegalovirus retinitis.

TABLE 1

Characteristics of patients receiving prior systemic chemotherapy

| | | |
|---|---|---|
| Patients entered | 35 | |
| Median Age | 36 | |
| Gender | M: 35, F: 0 | |
| KS Involvement | | |
| >50 mucocutaneous lesions | 20 (57%) | |
| Symptomatic edema | 27 (77%) | |
| Visceral Disease | 14 (40%) | |
| (Lung = 10; GI = 4) | | |
| Median CD 4 Count (/mm$^3$) | 5 | |
| Range | 0 to 230 | |
| Prior Opportunistic Infections | 23 (67%) | |
| Prior systemic therapy | | |
| ABV | 20 (57%) | |
| Vinca ± Bleomycin | 9 (25%) | |
| DaunoXome | 6 (17%) | |
| Two or more prior regimens | 14 (40%) | |

ABV = Adriamycin, Bleomycin, Vincristine, Vinca = Vincristine or Vinblastine
KS = Kaposi's sarcoma

TABLE 2

Toxicities, non-Hematologic n = 35

| | Grade ½ | Grade 3 | Grade 4 |
|---|---|---|---|
| Alopecia | 23[1] | | |
| Fatigue | 20 | | |
| Rash ± Pruritus | 14 | 0 | |
| Fevers | 10 | 2 | 0 |
| Myalgia | 10 | 0 | |
| Nausea/Vomiting | 10 | 0 | 0 |
| Diarrhea | 7 | 0 | 0 |
| Neuropathy | 6 | 0 | 0 |

Laboratory Toxicities

| | Grade 2 | Grade 3 | Grade 4 |
|---|---|---|---|
| Neutropenia | 8 (23%) | 5 (14%) | 7 (20%) |
| Anemia | 12 (34%) | 2 (6%) | 1 (3%) |
| Thrombocytopenia | 2 (6%) | 1 (3%) | 0 |

TABLE 3

Response Data

| | |
|---|---|
| Patients entered | 35 |
| Median Cycles given | 10 (range 1–22+) |
| Evaluable for response | 33 |
| Best Response attained | |
| Complete response | 0 |
| Partial response | 23 (66%) |
| Minimal response/stable disease | 12 (34%) |
| Progression | 0 |
| Median cycles to response | 5 (range 3–9) |
| Median duration of response | 5+ months |
| Range | 2 + −13.2 + months |
| Median Survival | not reached, in excess of 6 months |

Based on the preliminary results of these study, the activity of paclitaxel has been confirmed in patients who had received prior systemic chemotherapy. Of note, paclitaxel could be delivered to patients with advanced HIV disease who required multiple concurrent myelotoxic accents for prophylaxis or maintenance therapy of opportunistic infections.

Strata 2 of the study consisted of 20 patients with advanced AIDS-KS who had not received any prior systemic chemotherapy. The demographic characteristics and the results of treatment are provided below (Table 4–6).

TABLE 4

Patient Characteristics

| | |
|---|---|
| Patients entered | 20 |
| Median Age | 35 |
| Gender | M: 18, F: 2 |
| KS Involvement | |
| >50 mucocutaneous lesions | 17 (85%) |
| Symptomatic edema | 11 (55%) |
| Visceral Disease | 2 (10%) |
| GI = 2 | |
| Median CD 4 Count | 29 (range 0 to 247) |
| Prior Opportunistic Infections | 7 (35%) |

TABLE 5

| | Toxicities, non-Hematologic n = 20 | | |
|---|---|---|---|
| | Grade ½ | Grade 3 | Grade 4 |
| Alopecia | 15 | | |
| Fatigue | 7 | | |
| Rash ± Pruritus | 9 | 0 | |
| Fevers | 4 | 1 | 0 |
| Myalgia | 4 | 0 | |
| Nausea/Vomiting | 8 | 0 | 0 |
| Diarrhea | 6 | 0 | 0 |
| Neuropathy | 2 | 0 | 0 |

| | Laboratory Toxicities | | |
|---|---|---|---|
| | Grade 2 | Grade 3 | Grade 4 |
| Neutropenia | 4 (20%) | 2 (10%) | 3 (15%) |
| Anemia | 6 (30%) | 0 | 0 |
| Thrombocytopenia | 0 | 0 | 0 |

TABLE 6

| Response Data | |
|---|---|
| Patients entered | 20 |
| Median Cycles given | 6 (range 1–18+) |
| Evaluable for response | 19 |
| Best Response attained | |
| Complete response | 1 (5%) |
| Partial response | 12 (63%) |
| Minimal response/stable disease | 6 (32%) |
| Progression | 0 |
| Median cycles to response | 3 (range 3–9) |

These data show that paclitaxel is more effective therapeutically to KS compared to any other tumor studied thus far in the clinic. Furthermore the dosage and schedule used was extremely well tolerated. Aside from mild to moderate hair loss and occasional other mild toxicities, the lack of side effects is extraordinary.

Bone marrow suppression is common in AIDS. To counteract this immune deficiency, G-CSF is given if necessary. 43 of the patients in the clinical trial were evaluated for necessity for concomitant G-CSF and paclitaxel therapy.

TABLE 7

| G-CSF use (n = 43) | |
|---|---|
| Any G-CSF use | 30/43 (69%) |
| Required G-CSF prior to paclitaxel therapy | 16/43 (45%) |
| No G-CSF prior to paclitaxel therapy | 27/43 (55%) |
| Required G-CSF after start of paclitaxel therapy | 14/27 (52%) |
| Never required G-CSF | 13/27 (48%) |

Therefore out of the patients who were not on G-CSF prior to paclitaxel therapy, approximately 50% of them did not require G-CSF. This indicates that bone marrow suppression (including neutropenia) was not observed in these patients.

From the above examples, it can be seen that paclitaxel is therapeutically active at peak levels of 0.1–µM. The unwanted hematological and non-hematological side effects common in the prior art were absent when the peak levels were maintained at 15 hours or less. Myelosuppression was not observed at an $AUC_{(0 \to \infty)}$ of 1–4 µM/hour which corresponds to a three hour bolus of 50–100 mg/m² every 14 days. This effectiveness at lower doses is unexpected compared to the higher dose (135–225 mg/m²) of paclitaxel required in all other cancers studied thus far, including breast and ovarian. Further the treatment schedule of a 3 hour bolus every two weeks is novel. The reduced toxicity profile is particularly significant for patients with KS, who have many other concurrent complications of immunodeficiency and receive drugs with overlapping toxicities.

Compared to all previously studied drugs and combinations thus far, including liposomally encapsulated anthracyclines, the duration of response to paclitaxel as reflected by the median number of cycles tolerated by the study population with paclitaxel is two fold longer. The median number of cycles of paclitaxel given is 12 while in all other studies the cycle number is around 6–7. This indicates that paclitaxel is tolerated and therefore is useful at low doses as long-term therapy for KS.

What is claimed is:

1. A method of inhibiting neutropenia in a Kaposi's sarcoma patient being treated by long term administration of paclitaxel, said method comprising administering a dose of paclitaxel that induces a peak level of paclitaxel of about 0.1–1 µM and an $AUC_{(0 \to \infty)}$ of 1–4 µM/hour in a pharmaceutically acceptable carrier in a cycle of every 10–16 days for an excess of 4 cycles, wherein the paclitaxel is administered intravenously in a bolus not exceeding 3 hours.

2. The method of claim 1, wherein the dose intensity of paclitaxel is about 35 mg/m².

3. The method of claim 1, wherein the dose intensity of paclitaxel is about 75 mg/m².

4. The method of claim 1, wherein the cycle is about every 14 days.

5. The method of claim 1, wherein the number of cycles exceeds five.

6. The method of claim 1, wherein the paclitaxel bolus is administered for less than about 180 minutes.

7. The method of claim 1, wherein the $AUC_{(0 \to \infty)}$ is 1–3 µM/hour.

8. A method of inhibiting neutropenia in a Kaposi's sarcoma patient being treated by long term administration of paclitaxel, said method comprising administering a dose of paclitaxel between 35 and 75 mg/m² in a pharmaceutically acceptable carrier in a cycle of every 10–16 days for an excess of 4 cycles, wherein the paclitaxel is administered intravenously in a bolus not exceeding 3 hours.

9. A method of treating Kaposi's sarcoma in a human by long term administration of paclitaxel, said method comprising of:

(i) pre-treating of the patient with an anaphylaxis treatment agent selected from the group consisting of dexamethasone, cimetidine, and diphenhydramine hydrochloride;

(ii) administering paclitaxel so that a peak level of paclitaxel intravenously of about 0.1–1 µM is achieved every 10–16 days;

(iii) the $AUC_{(0 \to \infty)}$ is about 1–4 µM/hour; and (iv) said paclitaxel is administered in a bolus not to exceed about 180 minutes.

10. The method of claim 9, wherein the peak level of paclitaxel is achieved by a dose of paclitaxel of about 35 mg/m².

11. The method of claim 9, wherein the peak level of paclitaxel is achieved by a dose of paclitaxel of about 75 mg/m².

12. The method of claim 9, wherein the intravenous bolus of paclitaxel is given every 14 days.

13. The method of claim 9, wherein the administration of paclitaxel every 10–16 days is repeated for at least 4 cycles.

14. The method of claim 9, wherein the $AUC_{(0 \to \infty)}$ is about 1–3 μM/hour.

* * * * *